(12) United States Patent
Holler et al.

(10) Patent No.: US 11,554,130 B2
(45) Date of Patent: Jan. 17, 2023

(54) TREATMENT OF NEURODEGENERATIVE DISEASE WITH OVINE GM1 GANGLIOSIDOSIS GM1 GANGLIOSIDE

(71) Applicant: GlycoScience Research, Inc., Brookings, SD (US)

(72) Inventors: Larry D. Holler, Brookings, SD (US); Susan Holler, Brookings, SD (US)

(73) Assignee: Glycoscience Research, Inc., Brookings, SD (US)

( * ) Notice: Subject to any disclaimer, the term of this patent is extended or adjusted under 35 U.S.C. 154(b) by 185 days.

(21) Appl. No.: 16/741,254

(22) Filed: Jan. 13, 2020

(65) Prior Publication Data

US 2020/0222437 A1    Jul. 16, 2020

Related U.S. Application Data

(60) Provisional application No. 62/791,261, filed on Jan. 11, 2019.

(51) Int. Cl.
*A61K 31/702* (2006.01)
*A61P 25/28* (2006.01)
*A01K 67/02* (2006.01)
*A61K 35/12* (2015.01)

(52) U.S. Cl.
CPC ............ *A61K 31/702* (2013.01); *A01K 67/02* (2013.01); *A61K 35/12* (2013.01); *A61P 25/28* (2018.01)

(58) Field of Classification Search
CPC ........ A61K 31/702; A61K 35/12; A61P 25/28
See application file for complete search history.

(56) References Cited

U.S. PATENT DOCUMENTS

| | | | |
|---|---|---|---|
| 5,532,141 | A | 7/1996 | Holler |
| 5,698,763 | A | 12/1997 | Weissmann et al. |
| 9,023,812 | B2 | 5/2015 | Sipione et al. |
| 9,051,592 | B2 | 6/2015 | Ragaglia et al. |
| 9,394,558 | B2 | 7/2016 | Schneider et al. |
| 9,556,467 | B2 | 1/2017 | Ragaglia et al. |
| 2002/0158765 | A1 | 10/2002 | Pape et al. |
| 2006/0265773 | A1 | 11/2006 | Carroll et al. |
| 2008/0269183 | A1 | 10/2008 | Mellon et al. |
| 2009/0165154 | A1 | 6/2009 | Robi et al. |
| 2012/0035120 | A1 | 2/2012 | Defrees |
| 2012/0220763 | A1 | 8/2012 | Schneider et al. |
| 2012/0283199 | A1 | 11/2012 | Sipione et al. |
| 2014/0074742 | A1 | 3/2014 | Pratt |

FOREIGN PATENT DOCUMENTS

WO    2002081737 A2    10/2002

OTHER PUBLICATIONS

Alpaugh; EMBO Molecular Medicine (2017), 9; 1537-1557.*
Kavirajan et al., Lancet Neurol 2007; 6; 782-92.*
International Search Report dated Apr. 8, 2020 for PCT/US2020/013365.
Alpaugh et al., "Disease-modifying effects of ganglioside GM1 in Huntington's disease models", EMBO Mol Med., Oct. 9, 2017, vol. 9, No. 11, pp. 1537-1557.
"APHIS Factsheet: Scrapie Flock Certification Program: USDA Scrapie Programs", USDA, Jul. 31, 2009, pp. 1-3 Retrieved from https://www.alphis.usda.gov/publications/animal_health/content/printable_version/fs_scrafcp.pdf, on Mar. 4, 2020.
Jolly et al., "Genetic Disorders of Sheep in New Zealand: A Review and Perspective", New Zealand Veterinary Journal, Apr. 1, 2004, vol. 52, No. 2, pp. 52-64.
Kellar et al. "Risk Management of the Transmissible Spongiform Encephalopathies in North America", Revue Scientifique et Technique—Office International des Epizooties, Apr. 1, 2003, vol. 22, No. 1, pp. 201-221.
Prieur et al., "Animal Model of Human Disease", American Journal of Pathology, Dec. 31, 1991, vol. 139, No. 6, pp. 1511-1513.
Sullivan et al., "Commercialising Genetically Engineered Animal biomedical Products", Reproduction, Fertility & Development, Dec. 11, 2007, vol. 20, No. 1, pp. 61-66.

* cited by examiner

*Primary Examiner* — Pancham Bakshi
(74) *Attorney, Agent, or Firm* — Suiter Swantz pc llo

(57) ABSTRACT

A method of treating a symptom of neurodegenerative disease in a mammal subject includes administering a ganglioside preparation enriched in GM1, derived from an ovine animal afflicted with GM1 gangliosidosis. The ganglioside preparation is prepared through tissue isolation, extraction, and purification processes. The method includes the treatment of a symptom of Huntington's disease and other neurodegenerative diseases. A selective breeding method for producing a GM1 gangliosidosis-affected, scrapie-resistant ovine animal that produces substantially high tissue concentrations of GM1 ganglioside is described. A method to produce multiple successive generations of ovine animals to produce a GM1 gangliosidosis-affected, scrapie-resistant ovine animal and the production of additional generations to improve trait characteristics. The ganglioside product enriched in GM1 is extracted from an ovine animal that is GM1 affected and scrapie-resistant.

7 Claims, 15 Drawing Sheets

CARRIER/SCRAPIE RESISTANT (Gg/RR) RAM
×
CARRIER/NO SCRAPIE RESISTANCE (Gg/QQ) EWE

RAM

|  | EWE | | | |
|---|---|---|---|---|
|  | GQ | GQ | gQ | gQ |
| GR | GGQR | GGQR | GgQR | GgQR |
| GR | GGQR | GGQR | GgQR | GgQR |
| gR | GgQR | GgQR | ggQR | ggQR |
| gR | GgQR | GgQR | ggQR | ggQR |

25% NORMAL/SCRAPIE RESISTANT (GG/QR)
50% CARRIER/SCRAPIE RESISTANT (Gg/QR)*
25% AFFECTED/SCRAPIE RESISTANT (gg/QR)†

CARRIER/SCRAPIE RESISTANT (Gg/RR) RAM
×
NORMAL/NO SCRAPIE RESISTANCE (GG/QQ) EWE

RAM

|  | EWE | | | |
|---|---|---|---|---|
|  | GQ | GQ | GQ | GQ |
| GR | GGQR | GGQR | GGQR | GGQR |
| GR | GGQR | GGQR | GGQR | GGQR |
| gR | GgQR | GgQR | GgQR | GgQR |
| gR | GgQR | GgQR | GgQR | GgQR |

50% NORMAL/SCRAPIE RESISTANT (GG/QR)
50% CARRIER/SCRAPIE RESISTANT (Gg/QR)*

*USE FOR NEXT GENERATION BREEDING EWES ONLY
†USE FOR HARVEST

FIG. 3B

CARRIER/SCRAPIE RESISTANT (Gg/RR) RAM
×
CARRIER/SCRAPIE RESISTANT (Gg/QR) EWE

RAM \ EWE:

|  | GR | GQ | gR | gQ |
|---|---|---|---|---|
| GR | GGRR | GGQR | GgRR | GgQR |
| GR | GGRR | GGQR | GgRR | GgQR |
| gR | GgRR | GgQR | ggRR | ggQR |
| gR | GgRR | GgQR | ggRR | ggQR |

25% NORMAL/SCRAPIE RESISTANT (GG/RR or QR)
25% CARRIER/SCRAPIE RESISTANT (Gg/RR)*
25% CARRIER/SCRAPIE RESISTANT (Gg/QR)**
25% AFFECTED/SCRAPIE RESISTANT (ggRR, ggQR)†

---

CARRIER/SCRAPIE RESISTANT (Gg/RR) RAM
×
NORMAL/SCRAPIE RESISTANT (GG/QR) EWE

RAM \ EWE:

|  | GR | GQ | GR | GQ |
|---|---|---|---|---|
| GR | GGRR | GGQR | GGRR | GGQR |
| GR | GGRR | GGQR | GGRR | GGQR |
| gR | GgRR | GgQR | GgRR | GgQR |
| gR | GgRR | GgQR | GgRR | GgQR |

50% NORMAL/SCRAPIE RESISTANT (GG/RR) & (GG/QR)
25% CARRIER/SCRAPIE RESISTANT (Gg/RR)*
25% CARRIER/SCRAPIE RESISTANT (Gg/QR)**

*USE FOR NEXT GENERATION
**USE ONLY EWES FOR NEXT GENERATION
†USE FOR HARVEST

FIG. 3C

CARRIER/SCRAPIE RESISTANT (Gg/RR) RAM
× 
CARRIER/SCRAPIE RESISTANT (Gg/RR) EWE

RAM

|  | EWE | | | |
|---|---|---|---|---|
|  | GR | GR | gR | gR |
| GR | GGRR | GGRR | GgRR | GgRR |
| GR | GGRR | GGRR | GgRR | GgRR |
| gR | GgRR | GgRR | ggRR | ggRR |
| gR | GgRR | GgRR | ggRR | ggRR |

25% NORMAL/SCRAPIE RESISTANT (GG/RR)
50% CARRIER/SCRAPIE RESISTANT (Gg/RR)*
25% AFFECTED/SCRAPIE RESISTANT (gg/RR)†

*USE FOR NEXT GENERATION
†USE FOR HARVEST

CARRIER/SCRAPIE RESISTANT (Gg/RR) RAM
×
NORMAL/SCRAPIE RESISTANT (GG/RR) EWE

RAM

|  | EWE | | | |
|---|---|---|---|---|
|  | GR | GR | GR | GR |
| GR | GGRR | GGRR | GGRR | GGRR |
| GR | GGRR | GGRR | GGRR | GGRR |
| gR | GgRR | GgRR | GgRR | GgRR |
| gR | GgRR | GgRR | GgRR | GgRR |

50% NORMAL/SCRAPIE RESISTANT (GG/RR)
50% CARRIER/SCRAPIE RESISTANT (Gg/RR)*

FIG. 3D

TREATMENT OF NEURODEGENERATIVE DISEASE WITH OVINE GM1 GANGLIOSIDOSIS GM1 GANGLIOSIDE

CROSS-REFERENCE TO RELATED APPLICATIONS

The present application claims the benefit under 35 U.S.C. § 119(e) of U.S. Provisional Application Ser. No. 62/791,261, filed Jan. 11, 2019, which is hereby incorporated by reference in its entirety.

TECHNICAL FIELD

The present disclosure relates to compositions, methods and animals for the treatment of neurodegenerative disease, and particularly to treatment of Huntington's disease.

BACKGROUND

Neurodegenerative disease is an overarching term for a multitude of conditions which primarily affect neurons within the central nervous system (CNS). The progressive loss of neurons, or the loss of function of neurons, can result in a wide range of neurodegenerative symptoms that include cognitive, neuromuscular, and neuropsychiatric defects. Neurodegenerative diseases are incurable, with most therapeutic modalities centered around the easing of disease symptoms. Although not approved for human use, one class of compounds that may provide slowing or halting of neurodegenerative symptoms are gangliosides. Gangliosides belong to a class of glycolipids referred to as glycosphingolipids, which contain at least one neutral oligosaccharide residue at the polar head of a lipid molecule. Specifically, gangliosides contain at least one sialic acid residue in this oligosaccharide head. These sialic acid residues give the head, and the glycolipid molecule itself, a net negative charge. The charge and structure of gangliosides may facilitate the easing of disease symptoms through several mechanisms, including inhibition of aberrant protein aggregation, a hallmark of many neurodegenerative diseases.

Huntington's Disease (HD) is a fatal, inherited, neurodegenerative disorder characterized by progressive neuromuscular, neuropsychiatric, and cognitive decline. About 30,000 people in the United States currently have symptomatic HD disease, while another 75,000 individuals will eventually develop HD symptoms, with an average age of onset of 39 years. There is no cure for HD. However, treatment of model animals with gangliosides, has been shown to reduce symptoms for several neurodegenerative diseases, including HD.

Currently, synthetic production of therapeutic doses of GM1 for use in neurodegenerative disease is not economically feasible. Traditional sources of GM1 (i.e., bovine) are not utilized due to dangers of transmission of the infectious prion agent that causes bovine spongiform encephalopathy, PrP. Another disadvantage of bovine sources is that although the source provides a more plentiful resource for GM1 than synthetic methods, the purification process still requires the processing of considerably large amounts of neural tissue. Therefore, it would be desirable to utilize an animal that produces high tissue concentrations of GM1 for harvest that also poses a low risk of transmittal of disease for humans.

SUMMARY

A method for the treatment of a symptom of neurodegenerative disease in a mammal subject is disclosed in accordance with one or more embodiments of the present disclosure. In one embodiment, the method includes administering to a mammal subject a therapeutic quantity of a ganglioside preparation substantially enriched in GM1. In one embodiment, the ganglioside preparation is derived from an ovine animal harboring a scrapie-resistant genotype. In another embodiment, the ovine animal is afflicted with GM1 gangliosidosis. In another embodiment, the ganglioside preparation enriched in GM1 is prepared by isolating ganglioside-rich tissues from the ovine animal afflicted with GM1 gangliosidosis. In another embodiment, the ganglioside preparation enriched in GM1 is further prepared by extracting gangliosides from ganglioside-rich tissues using extraction methods and extraction agents. In another embodiment, the ganglioside preparation enriched in GM1 is further prepared by purifying the GM1 from the extracted gangliosides through chromatographic methods, or other methods.

A selective breeding method for producing an ovine animal harboring a scrape-resistant genotype originating from a certified scrapie-free flock that is afflicted with GM1 gangliosidosis, producing substantially high amounts of GM1 and is robust at harvest to satisfy abattoir guidelines is disclosed, in accordance with one or more embodiments of the present disclosure. In one embodiment, the method includes selectively breeding a first generation (F1) that are carriers of GM1 gangliosidosis and harbor a scrapie-resistant genotype. In another embodiment, the F1 generation is produced by identifying and selecting female and/or male ovine animals that are carriers of GM1 gangliosidosis through at least one of genetic testing or the measurement of GM1 levels in GM1 gangliosidosis afflicted offspring. In another embodiment, the F1 generation is further produced through identifying male or female ovine animals harboring a scrapie resistant genotype through genetic testing. In another embodiment, the F1 generation is further produced by mating ovine animals that are carriers of GM1 gangliosidosis with ovine animals harboring the scrapie resistance genotype to generate members of an F1 family that are carriers of GM1 gangliosidosis and harbor scrapie resistance allele(s). In another embodiment, the F1 generation is further produced by identifying offspring that produce substantially high amounts of GM1 and are robust at harvest to satisfy abattoir guidelines. In another embodiment, the method includes selectively breeding a second generation (F2). In another embodiment, selectively breeding a F2 generation includes mating members of the F1 generation that are carriers of GM1 gangliosidosis and harbor the scrapie-resistant genotype with animals that harbor the scrapie-resistant genotype and are carriers or non-carriers of GM1 gangliosidosis. In another embodiment, selective breeding of the F2 generation consists of identifying offspring that harbor the scrapie resistance gene and are affected by (or are carriers or non-carriers of) GM1 gangliosidosis. In another embodiment, the F2 generation is further produced by identifying offspring from the mated ovine animals that produce substantially high amounts of GM1 and are robust at harvest to satisfy abattoir guidelines.

In another embodiment, ovine animals in this method continue to be selectively mated over five or more generations as to produce scrapie-resistant, GM1 gangliosidosis-affected ovine animals with substantially high concentrations of GM1 in the central nervous system (CNS) tissue of the animal, while being robust enough to satisfy abattoir guidelines. In another embodiment, the gangliosidosis-affected ovine animal will produce more than 10.0 grams of GM1 per kilogram of central nervous system (CNS) tissue.

A method for inhibiting the levels of a neurodegenerative disease-associated protein in a mammal subject is disclosed, in accordance with one or more embodiments of the present disclosure. In one embodiment, the method includes administering to a mammal subject a therapeutic dose of a ganglioside preparation for the treatment of neurodegenerative disease symptoms. In one embodiment, the method includes treating with a ganglioside preparation substantially enriched in GM1. In another embodiment, the method includes treating with a ganglioside preparation enriched in GM1, derived from an ovine animal harboring a scrapie-resistant genotype. In another embodiment, the ovine animal is afflicted with GM1 gangliosidosis. In another embodiment, the ganglioside preparation enriched in GM1 is prepared by isolating ganglioside-rich tissues from the ovine animal afflicted with GM1 gangliosidosis. In another embodiment, the ganglioside preparation enriched in GM1 is further prepared by extracting gangliosides from ganglioside-rich tissues using extraction methods and extraction agents. In another embodiment, the ganglioside preparation enriched in GM1 is further prepared by purifying the GM1 from the extracted gangliosides through chromatographic methods, or other methods.

It is to be understood that both the foregoing general description and the following detailed description are exemplary and explanatory only and are not necessarily restrictive of the invention as claimed. The accompanying drawings, which are incorporated in and constitute a part of the specification, illustrate embodiments of the invention and together with the general description, serve to explain the principles of the invention.

BRIEF DESCRIPTION OF THE DRAWINGS

The numerous advantages of the disclosure may be better understood by those skilled in the art by reference to the accompanying figures in which:

FIG. 3B illustrates Punnett squares detailing the predicted results of a cross between a GM1 gangliosidosis-carrier, homozygous scrapie-resistant, (Gg/RR) animal with a GM1 gangliosidosis carrier or GM1 gangliosidosis free, scrapie-susceptible (Gg/QQ or GG/QQ) animal, in accordance with the present disclosure;

FIG. 3C illustrates Punnett squares detailing the predicted results of a cross between a GM1 gangliosidosis carrier, homozygous scrapie-resistant (Gg/RR) animal with a GM1 gangliosidosis carrier or GM1 gangliosidosis clear, heterozygous scrapie-resistant (Gg/QR or GG/QR) animals, in accordance with the present disclosure;

FIG. 3D illustrates a Punnett square detailing the predicted results of a cross between a GM1 gangliosidosis carrier, homozygous scrapie-resistant (Gg/RR) animal with GM1 gangliosidosis carrier or GM1 gangliosidosis clear, homozygous scrapie-resistant (Gg/RR GG/RR) animals, in accordance with the present disclosure;

DETAILED DESCRIPTION

Figure 1:
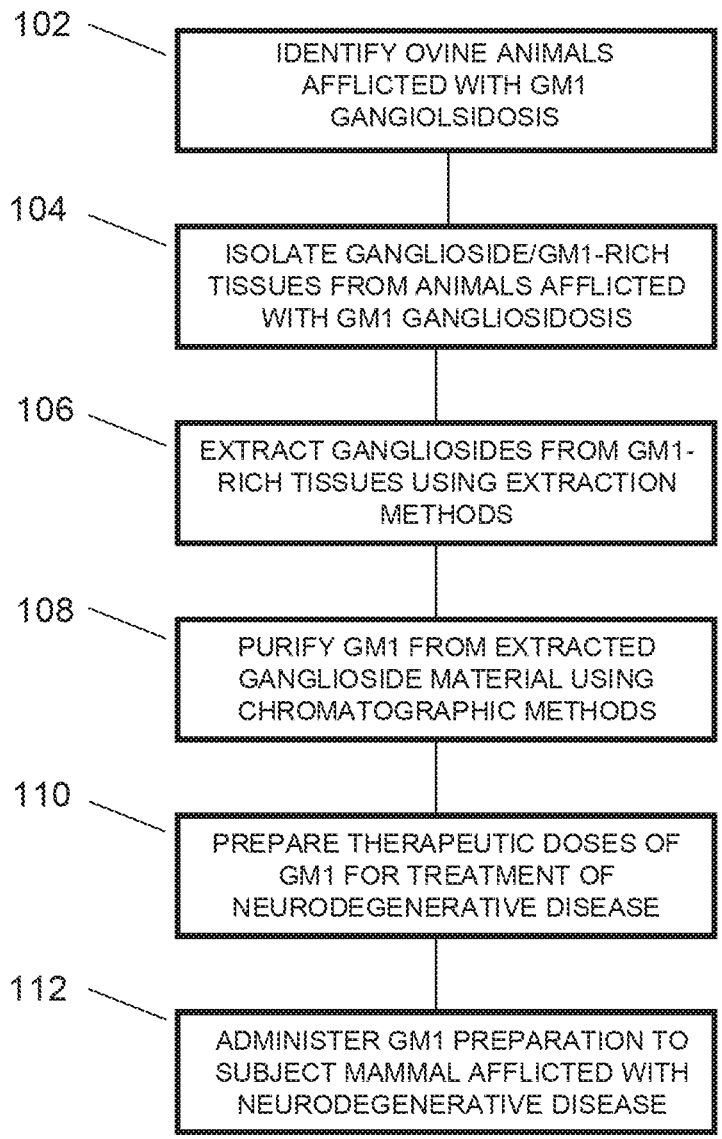
FIG. 1 illustrates a process flow diagram of a method for treating a subject afflicted with neurodegenerative disease with a therapeutic amount of GM1 derived from an ovine animal afflicted with GM1 gangliosidosis, in accordance with the present disclosure.

The present disclosure has been particularly shown and described with respect to certain embodiments and specific features thereof. The embodiments set forth herein are taken to be illustrative rather than limiting. It should be readily apparent to those of ordinary skill in the art that various changes and modifications in form and detail may be made without departing from the spirit and scope of the disclosure.

Reference will now be made in detail to the subject matter disclosed, which is illustrated in the accompanying drawings.

Referring generally to FIGS. 1 through 7C, a method of treating a symptom of neurodegenerative disease in a subject is disclosed, in accordance with one or more embodiments of the present disclosure. Embodiments of the present disclosure are directed to the administering of the mammal subject afflicted with neurodegenerative disease a preparation enriched in GM1, derived from an ovine animal afflicted with GM1 gangliosidosis. Additional embodiments are also directed to a method for the treating of a symptom of Huntington's disease (HD). Embodiments of the present disclosure are directed to the administering of the mammal subject afflicted with HD a preparation enriched in GM1, derived from an ovine animal afflicted with GM1 gangliosidosis. Additional embodiments are directed to a selective breeding method for producing a scrapie-resistant ovine animal afflicted with GM1 gangliosidosis that produces substantially high amounts of GM1 and is robust to satisfy abattoir guidelines for harvest. Additional embodiments are also directed to a composition enriched in GM1 isolated from a scrapie-resistant ovine animal, and to a method for inhibiting a level of a neurodegenerative disease-associated protein in a mammal subject.

It is noted herein that a mammal subject refers to any mammal with the capability of developing neurodegenerative disease. Mammals known to naturally develop neurodegenerative diseases include, but are not limited to, humans, horses, dogs, and cats. Animal models known to develop neurodegenerative disease include, but are not limited to, mice, rats and rhesus monkeys. Neurodegenerative disease involves any pathological process involving the loss of neurons, or the loss of function of neurons, within the central nervous system (i.e., brain and spinal cord) that result in cognitive, neuromuscular, and/or neuropsychiatric defects. Examples of neurodegenerative diseases include, but are not limited to, Alzheimer's disease, Parkinson's disease, prion disease, motor neuron disease, Huntington's disease, amyotrophic lateral disease, spinocerebellar disease and spinal muscular atrophy. Neurodegenerative disease may also be a result of damage relating to viral, bacterial, or other infectious agents, including but not limited to HIV, influenza viruses, *Chlamydia pneumoniae*, and herpes viruses. Neurodegenerative disease may also be a result of trauma received by the individual, including but not limited to traumatic brain injury (TBI), chronic traumatic encephalopathy (CTE), and spinal cord injury.

A method for obtaining lipid gangliosides from animals afflicted with GM1 gangliosidosis is generally described in U.S. Pat. No. 5,532,141, issued on Jul. 2, 1996, which is incorporated herein by reference in the entirety.

FIG. 1 illustrates steps in a method 100 for treating a subject afflicted with neurodegenerative disease with GM1, in accordance with the present disclosure. In an embodiment, the method 100 includes the step 102 of identifying an ovine animal with GM1 gangliosidosis. For example, identifying an ovine animal with GM1 gangliosidosis may include identifying ovine animals that have developed symptoms of GM1 gangliosidosis (e.g., ataxia). In another example, the identification of ovine animals with GM1 gangliosidosis includes genetic testing using any genetic test known in the art. For instance, the genetic testing may include genetic sequencing of the 3-galactosidase gene (GLB1). In another instance, the genetic testing includes probing of the GLB1 gene using restriction fragment length polymorphism (RFLP) assays. Genetic testing may also include any other genetic testing method including but not limited to PCR, real-time PCR, or other nucleic acid amplification method.

In some embodiments, the method 100 includes the step 104 of isolating ganglioside and/or GM1-rich tissues from animals afflicted with GM1 gangliosidosis. Ganglioside and GM1-rich tissues typically include the CNS, (i.e., brain and spinal cord). Initial tissue removal typically occurs at the abattoir, or slaughterhouse. However, tissue removal may also occur at a site other than an abattoir. To harvest and isolate ganglioside and/or GM1-rich tissues, ovine animals are euthanized humanely through methods including, but not limited to, electrical stunning and exsanguination. CNS tissues are then removed rapidly and stored at −10 to −20° C. until use. In another embodiment, the method for obtaining GM1 includes the harvesting of non-CNS tissues. The non-CNS tissues include peripheral nervous tissue, solid organs, connective tissue, vasculature, or any other tissue within the ovine animal where GM1 may be extracted.

In some embodiments, the method 100 includes the step 106 of extracting gangliosides from GM1-rich tissues using extraction methods. For example, the extraction methods include the use of organic reagents (e.g., chloroform, methanol, dichloromethane, acetone, tetrahydrofuran and/or any other organic solvent used in chemical extractions) as well as nonorganic reagents (e.g., water). Methods for extraction of GM1 from GM1-rich tissues further include those as reported by Holler in U.S. Pat. No. 5,532,141, issued on Jul. 2, 1996, which has been incorporated by reference in the entirety. For example, frozen tissues are thawed, and homogenized in twenty volumes of chloroform:methanol (C:M 1:1) to a final ratio of 10:10:1 (C:M:water), to extract total lipids. The homogenates are stirred continuously for 12 hours, and supernatants are cleared, using centrifugation (1000×g), and then collected. Residues are extracted for four hours in 10 volumes of C:M (2:1), after which supernatants are combined, and evaporated to dryness on a rotary evaporator. The residue is dissolved in C:M (2:1), and any phospholipids in the solute are hydrolyzed by adding an appropriate volume of 1M KOH (in methanol), at room temperature for 12 hours. The KOH is neutralized with glacial acetic acid, and the resulting mixture is evaporated to dryness in a rotary evaporator.

In some embodiments, the method 100 includes the step 108 of purifying GM1 from extracted ganglioside material using chromatographic methods. For example, the extracted GM1-rich material may be applied (e.g., bound to) a solid phase column, with the addition of various solvents removing various species of compounds from the solid phase column, creating many fractions containing various ganglioside species and purities of ganglioside species (e.g., including GM1). Columns used in chromatographic purification include, but are not limited to, C18 solid phase extraction columns, Sephadex columns, DEAE-Sephadex columns, silica gel columns, Q-Sepharose columns, MonoQ columns, and strong anion exchanger (SAX) columns. For example, the extracted gangliosides are desalted via reverse phase liquid chromatography (RPLC), on a C18 column. Lipids are eluted from the column with C:M (2:1), and additional volumes of methanol. Pooled eluates are evaporated to dryness, and then resolubilized in methanol.

In another example, the neutral glycosphingolipids and gangliosides are separated from each other via ion exchange chromatography on a DEAE-Sephadex-A-25 column converted to acetate form. The resins are batch washed, three times, in 5 volumes of C:M:4M sodium acetate (30:60:8, v/v/v), and the resulting suspension is allowed to stand for at least 12 hours. Any resulting supernatant is discarded, and the resin is again batch washed three times with 5 volumes of C:M:water, (30:60:8 v/v/v). Washed resin is then poured into an appropriate diameter glass column fitted with sand-overlayered glass wool retainers. Each sample is loaded on an individual column, in a minimal volume of methanol. The neutral glycolipids were eluted in approximately 5 column volumes of methanol, while gangliosides were eluted off the column with five column volumes of 0.5 M ammonium acetate in methanol. Ganglioside fractions were diluted with water, desalted, and evaporated to dryness. Total gangliosides were then dissolved in C:M (1:1), and stored at −40° C. to prevent evaporation.

Following the separation of total gangliosides, the products are qualitated and quantitated using thin layer chromatography. For example, an aliquot of each total ganglioside fraction (about 1.0 g wet weight for each) is applied with a TLC spotter to glass backed HPTLC plates (10×20 cm). The gangliosides are separated in a mixture of chloroform/methanol/25% CaCl (50:40:10 v:v:v). The mobile phase is allowed to travel to within 1 cm of the top of the plate. The plates are air dried for at least 10 minutes, and then sprayed with resorcinol-HCl reagent, then covered with a clean glass plate, and heated in an oven at 110° C., for 7-10 minutes.

In another embodiment, the method 100 includes the step 110 of preparing a therapeutic dose of GM1 for treatment of neurodegenerative disease. For example, the GM1 may be prepared for intramuscular, subcutaneous, or intravenous use. In another example, the GM1 is prepared for intranasal use. In another example, the GM1 is prepared for intrathecal use, intraspinal use, or any other preparation that would allow delivery of the therapeutic preparation into the CNS. It should be noted that for each modality of use the therapeutic dose of GM1 may require differing formulations (e.g., solvents, preservatives, and/or salts) and different concentrations and total amounts of GM1.

In another embodiment, the method 100 includes the step 112 of administering a therapeutic quantity (e.g., dose) of the GM1 preparation to the subject mammal afflicted with neurodegenerative disease. For example, the administration of the therapeutic quantity of the GM1 preparation may be performed intramuscularly, subcutaneously, or intravenously. In another example, the administration of the therapeutic dose of the GM1 preparation may be performed intranasally. In another example, administration of the therapeutic dose of the GM1 preparation may be performed intrathecally, intraspinally, or any other administration that allows delivery of the therapeutic preparation into the CNS.

In one embodiment, the ovine animal afflicted with GM1 gangliosidosis harbors a scrapie-resistant genotype. In another embodiment, the scrapie-resistant genotype is identified through genetic testing. In another embodiment, the scrapie-resistant genotype is identified through genetic testing approved by the USDA Scrapie Free Flock Certification Program (SFCP). In another embodiment, the ovine animal harboring a scrapie-resistant genotype may originate from an export category flock of the USDA Scrapie Free Flock Certification Program (SFCP). Ovine animals afflicted with GM1 gangliosidosis and harboring a scrapie free genotype may also originate from USDA-like scrapie certification programs from other countries, such as the Canadian Voluntary Scrapie Flock Certification Program, and the Australian TSE Freedom Assurance Project, or other national scrapie certification program.

It is noted herein that the prion-causing scrapie disease, although not known to be communicable to humans, nonetheless requires that ovine animals be certified prion-free before ovine products can be approved for medicinal use in humans. Scrapie resistance genotypes in ovine animals generally refers to codons 136, 154 and 171 of the prion protein (PrP) encoded by the ovine prion gene, wherein codon 171 is the codon of most importance. Ovine animals that harbor a glutamine residue at codon 171 (171QQ) in both alleles of the prion protein gene are susceptible to scrapie disease. Ovine animals that harbor an arginine residue at codon 171 (171RR or 171QR) in one or both alleles of the prion protein gene are considered resistant to scrapie disease. Ovine animals that harbor a 136AA/171QR or 136AV/171QR genotype may also be considered resistant to scrapie disease. Scrapie-resistant genotypes may also include other combinations involving codons 136, 154, and 171 not listed here.

In another embodiment, administering of GM1 in a subject increases the subject's life expectancy. In another embodiment, administration of GM1 is performed prophylactically, before the mammal subject exhibits symptoms of neurodegenerative disease. It is noted herein that the age of onset for neurodegenerative disease is typically late adulthood but, in some instances, can occur as early as childhood. The biological processes that result in the onset of neurodegenerative disease likely occur at a considerably earlier age. Prophylactic use of GM1 may therefore delay the onset of disease in those patients known to have a genetic susceptibility to neurodegenerative disease, or that have had recent CNS infections or trauma.

In another embodiment, the symptoms of neurodegenerative disease may include a cognitive symptom. For example, cognitive symptoms may include dementia, delusion, or amnesia. In another embodiment, the symptoms of neurodegenerative disease may include a neuromuscular symptom. For example, neuromuscular symptoms may include ataxia, hypokinesia, dystonia, or chorea. In another embodiment, the symptoms of neurodegenerative disease may include neuropsychiatric symptoms. For example, neuropsychiatric symptoms may include anxiety, depression, aggression, or compulsive behavior. Other cognitive, neuromuscular or neuropsychiatric symptoms listed here may also be a symptom of neurodegenerative disease. Therefore, the above description should not be interpreted as a limitation of the present disclosure, but merely an illustration.

Figure 2:
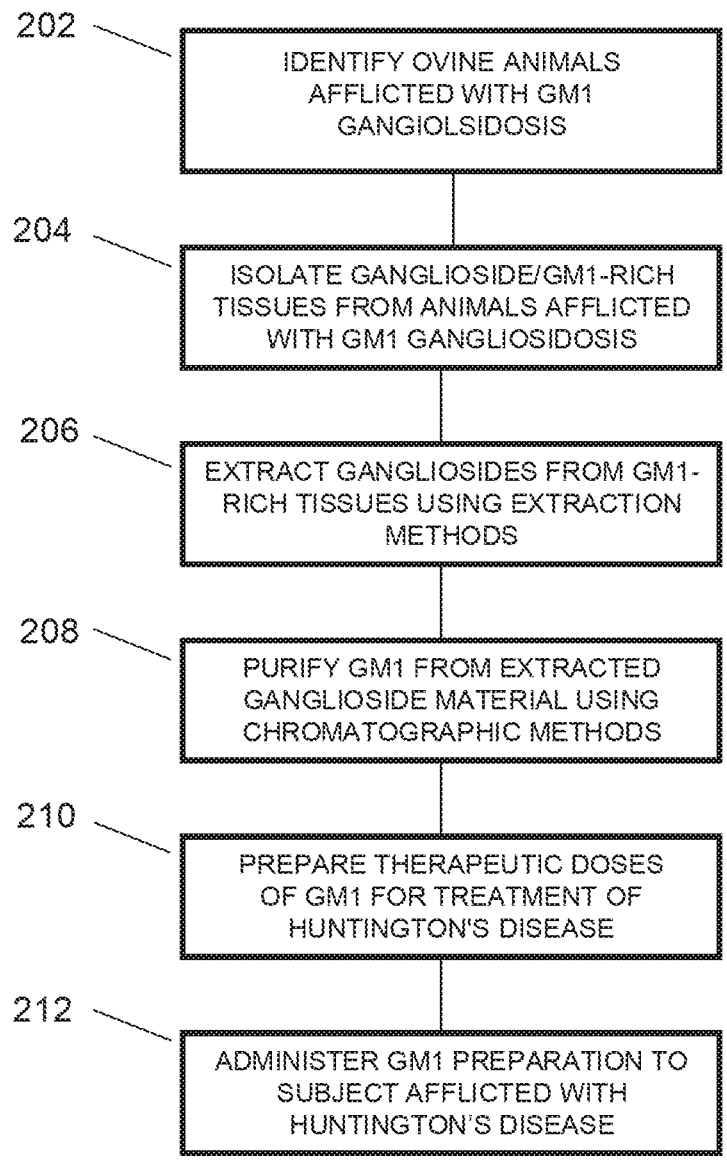
FIG. 2 illustrates a process flow diagram of a method for treating a subject afflicted with Huntington's disease with a therapeutic amount of GM1 derived from an ovine animal afflicted with GM1 gangliosidosis, in accordance with the present disclosure.
Figure 3A:
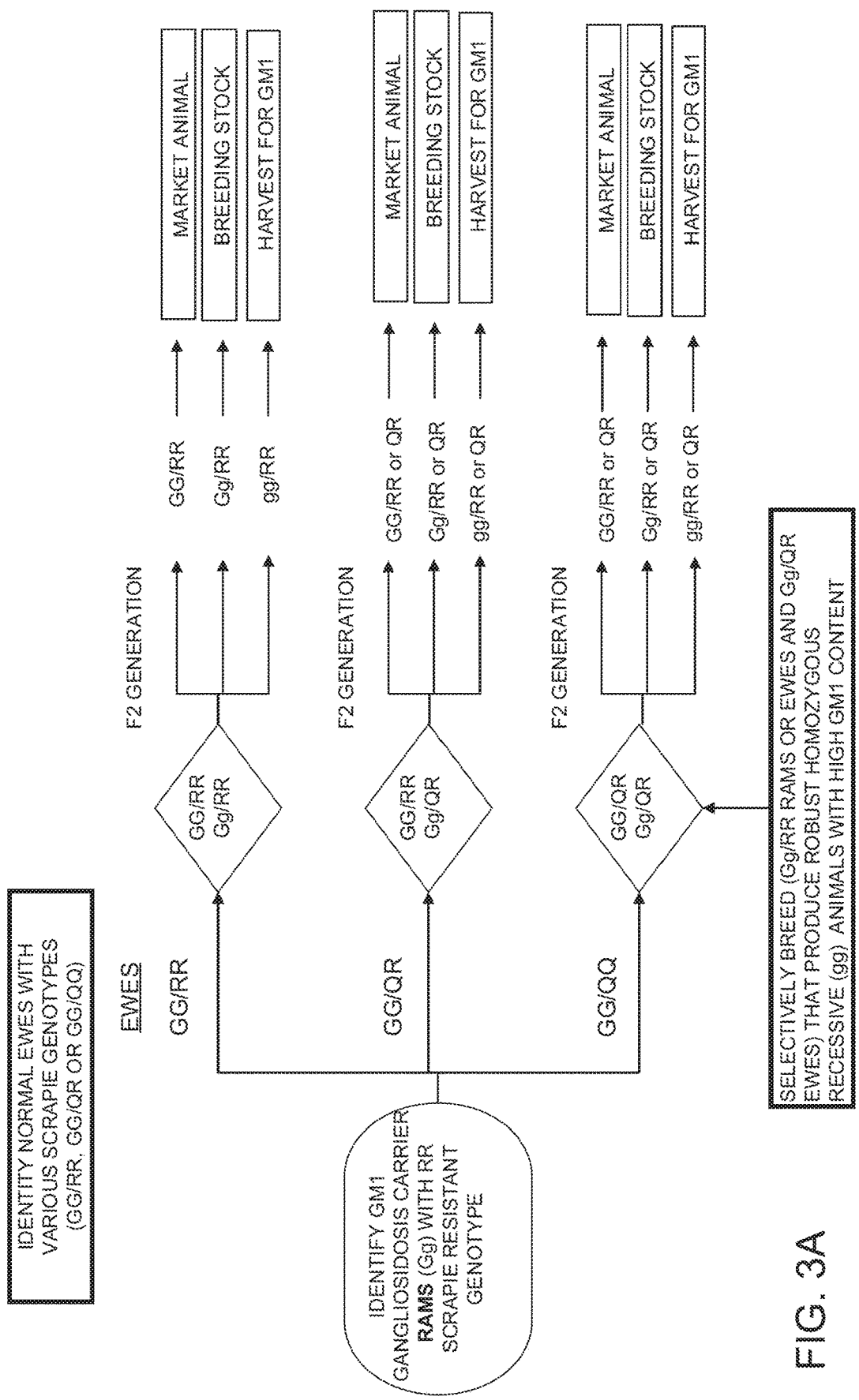
FIG. 3A illustrates a flow chart detailing the method for producing a scrapie-resistant, GM1 gangliosidosis-affected ovine animal possessing high concentrations of GM1 and robust enough to satisfy abattoir guidelines, in accordance with the present disclosure.

FIG. 2 illustrates a method 200 for treating a subject afflicted with Huntington's disease (HD) with GM1, in accordance with the present disclosure. In one embodiment, method 200 includes the step 202 of identifying an ovine animal afflicted with GM1 gangliosidosis. As detailed above, the identification of ovine animals with GM1 gangliosidosis includes identifying ovine animals that have developed symptoms of GM1 gangliosidosis (e.g., ataxia). In another embodiment, the identification of ovine animals with GM1 gangliosidosis includes genetic testing. In another embodiment, the genetic testing includes genetic sequencing of the β-galactosidase gene (GLB1). In another embodiment, the genetic testing includes, but is not limited to probing of the GLB1 gene using restriction fragment length polymorphism (RFLP) assays, PCR assay, real time PCR assays, or any other DNA amplification method.

In another embodiment, the method 200 includes the step 204 of isolating GM1 and/or ganglioside rich tissues from an ovine animal afflicted with GM1 gangliosidosis (e.g., removal of brain and/or spinal cord). In another embodiment, the method 200 includes the step 206 of extracting gangliosides from GM1 and/or gangliosides from enriched tissues using extraction methods. In another embodiment, the method 200 includes the step 208 of purifying GM1 from the extracted ganglioside material using chromatographic or other methods. Detailed methods for the extraction and purification of GM1 are detailed herein.

It is noted herein that mammal subject refers to any mammal with the capability of developing HD. Mammals known to naturally develop HD include, but are not limited to, humans. Animal models known to develop neurodegenerative disease include, but are not limited to, mice, rats and rhesus monkeys. It is noted herein that HD is an autosomal dominant disease that is the result of and expanded trinucleotide (CAG) repeat on one or both alleles of the Huntingtin gene (HTT).

In another embodiment, method 200 includes the step 210 of preparing therapeutic doses of isolated GM1 for the treatment of HD. For example, the GM1 may be prepared for intramuscular, subcutaneous, or intravenous use. In another example, the GM1 may be prepared for intranasal use. In another embodiment, the GM1 may be prepared for intrathecal use, intraspinal use, or any other preparation that would allow delivery of the therapeutic preparation into the CNS.

In another embodiment, the method 200 includes the step 212 of administering the therapeutic dose of the GM1 preparation to a subject afflicted with HD. For example, the administration of the therapeutic dose of the GM1 preparation may be performed intramuscularly, subcutaneously, or intravenously. In another example, the administration of the therapeutic dose of the GM1 preparation may be performed intranasally. In another example, the administration of the therapeutic dose of the GM1 preparation may be performed intrathecally, intraspinally, or any other administration that allows delivery of the therapeutic preparation into the CNS.

In another embodiment, the symptoms of HD may include a cognitive symptom. For example, cognitive symptoms may include dementia, delusion, or amnesia. In another embodiment, the symptoms of HD may include a neuromuscular symptom. For example, neuromuscular symptoms may include ataxia, hypokinesia, dystonia, or chorea. In another embodiment, the symptoms of HD may include neuropsychiatric symptoms. For example, neuropsychiatric symptoms may include anxiety, depression, aggression, or compulsive behavior. Other cognitive, neuromuscular or neuropsychiatric symptoms listed here may also be a symptom of HD. Therefore, the above description should not be interpreted as a limitation of the present disclosure, but merely an illustration.

In one embodiment, the ovine animal afflicted with GM1 gangliosidosis harbors a scrapie-resistant genotype. In another embodiment, the scrapie-resistant genotype is identified through genetic testing. It is noted herein that genetic testing for the scrapie-resistant genotype may include DNA sequencing, RFLP analysis, or any other testing as typically required to determine the scrapie-resistant genotype. In another embodiment, the ovine animal harboring a scrapie-resistant genotype may originate from an export category flock that is monitored by the United States Department of Agriculture (USDA) Scrapie Free Flock Certification Program (SFCP) or similar program for monitoring scrapie disease.

Referring to FIG. 3A, a selective breeding method 300 for producing an ovine animal harboring a scrapie-resistant genotype from a certified scrapie-free flock that is afflicted with GM1 gangliosidosis, produces substantially high amounts of GM1, and is robust to satisfy abattoir guidelines is disclosed, in accordance with one or more embodiments of the present disclosure. The method includes selectively producing an F1 generation. In an embodiment, the production of a first F1 generation includes identifying male and/or female ovine animals that are carriers of GM1 gangliosidosis (Gg) through at least one of genetic testing or the measurement of GM1 levels in GM1 gangliosidosis-afflicted offspring. It is noted herein that the wild type, or normal, allele for the GLB1 gene is noted by the capital "G", and that the mutated allele of GLB1 that is implicated in GM1 gangliosidosis is noted by the lower case "g". In another embodiment, production of a first F1 generation includes identifying male and/or female ovine animals harboring a scrapie resistance genotype (RR) through genetic testing. It is noted herein that an allele that imparts resistance to scrapie is noted by a capital "R", whereas an allele that does not impart resistance to scrapie is noted by "Q". In another embodiment, the production of a first F1 generation includes mating ovine animals that are carriers of GM1 gangliosidosis (Gg) with ovine animals harboring the scrapie resistance genotype (RR) to generate an F1 generation that are carriers of GM1 gangliosidosis and harbor the homozygous scrapie-resistance genotype (Gg/RR) or the heterozygous scrapie-resistance genotype (Gg/QR). FIG. 3B refers to a Punnett square detailing the genotypic possibilities and probabilities of an F1 generation produced from a GM1 gangliosidosis-carrier, homozygous scrapie-resistant (Gg/RR) animal with a GM1 gangliosidosis carrier or GM1 gangliosidosis clear, scrapie-susceptible (Gg/QQ or GG/QQ) animal. It should be noted that all rams harbor the scrapie resistant RR genotype so that all offspring will contain at least one scrapie-resistant allele.

Crossing a GM1 gangliosidosis-carrier, homozygous scrapie-resistant (Gg/RR) animal with a GM1 gangliosidosis carrier, scrapie-susceptible (Gg/QQ) animal will result in three genotypes. Half of the animals will be GM1 gangliosidosis carriers that are heterozygous scrapie resistant, while the rest of the animals will be evenly split between GM1 gangliosidosis clear (GG) and GM1 gangliosidosis affected (gg) animals that are heterozygous scrapie-resistant.

Crossing a GM1 gangliosidosis-carrier, homozygous scrapie-resistant (Gg/RR) animal with a GM1 gangliosidosis clear, scrapie-susceptible (GG/QQ) animal will result in two genotypes at equal proportions. Half of the animals will acquire a GM1 gangliosidosis clear/heterozygous scrapie-resistant genotype (GG/QR), whereas, the other half will acquire a GM1 gangliosidosis carrier/heterozygous scrapie-resistant genotype (Gg/QR). It is noted herein that the initial ovine animal identified as a carrier for GM1 gangliosidosis (Gg) may also carry heterozygous (QR) or homozygous (RR) scrapie resistance. Since GM1 gangliosidosis is a rare disease in ovine animals, there is a reduced selection of scrapie-resistant genotypes in GM1 gangliosidosis-affected ovine animals than in wild type ovine animals, which may therefore require production of F1, F2, or more generations in order to arrive at a generation that produces animals with a GM1 gangliosidosis-afflicted, scrapie-resistant (gg/QR or gg/RR) genotype.

In another embodiment, the selective breeding method may include mating GM1 gangliosidosis carrier/homozygous scrapie-resistant (Gg/RR) ovine animals with GM1 gangliosidosis carrier or GM1 gangliosidosis-clear animals that are heterozygous scrapie-resistant (GG/QR or Gg/QR). FIG. 3C refers to Punnett squares detailing the genotypic possibilities and probabilities of animals produced from mating of GM1 gangliosidosis carrier/homozygous scrapie-resistant (Gg/RR) ovine animals with GM1 gangliosidosis carrier or GM1 gangliosidosis-clear animals that are heterozygous scrapie-resistant (GG/QR or Gg/QR).

The cross between GM1 gangliosidosis carrier/homozygous scrapie-resistant (Gg/RR) ovine animals with GM1 gangliosidosis carrier animals that are heterozygous scrapie-resistant (Gg/QR) is predicted to produce six different genotypes, including GM1 gangliosidosis carrier/heterozygous and homozygous scrapie-resistant (Gg/RR) genotypes that may be used as breeding stock for the next generation. GM1 gangliosidosis affected animals (gg/QR and gg/RR) will also be produced and later harvested for GM1.

The cross between GM1 gangliosidosis carrier/homozygous scrapie-resistant (Gg/RR) ovine animals with GM1 gangliosidosis clear animals that are heterozygous scrapie-resistant (GG/QR) is predicted to produce four different genotypes, including GM1 gangliosidosis carrier/heterozygous and homozygous scrapie-resistant (Gg/RR) genotypes that may be used as breeding stock for the next generation.

In another embodiment, the selective breeding method may include mating GM1 gangliosidosis carrier/homozygous scrapie-resistant (Gg/RR) ovine animals with GM1 gangliosidosis carrier or GM1 gangliosidosis clear animals that are homozygous scrapie-resistant (GG/RR or Gg/RR). FIG. 3D refers to Punnett squares detailing the genotypic possibilities and probabilities of animals produced from mating of GM1 gangliosidosis carrier/homozygous scrapie-resistant (Gg/RR) ovine animals with GM1 gangliosidosis carrier or GM1 gangliosidosis-clear animals that are homozygous scrapie-resistant (GG/RR or Gg/RR).

The cross between GM1 gangliosidosis carrier/homozygous scrapie-resistant (Gg/RR) ovine animals with GM1 gangliosidosis carrier animals that are heterozygous scrapie-resistant (Gg/RR) is predicted to produce three different genotypes, including GM1 gangliosidosis carrier/homozygous scrapie-resistant (Gg/RR) genotypes that may be used as breeding stock for the next generation. GM1 gangliosidosis affected animals (gg/RR) will also be produced and later harvested for GM1.

The cross between GM1 gangliosidosis carrier/homozygous scrapie-resistant (Gg/RR) ovine animals with GM1 gangliosidosis clear animals that are homozygous scrapie-resistant (GG/RR) is predicted to produce two different genotypes, including GM1 gangliosidosis carrier/homozygous scrapie-resistant (Gg/RR) genotypes that may be used as breeding stock for the next generation.

In another embodiment, the selective breeding method includes selectively breeding ovine animals over five or more generations so as to produce GM1 gangliosidosis-affected offspring with substantially high amounts of GM1 and are robust so as to satisfy abattoir guidelines. In another embodiment, the selective breeding will produce scrapie-resistant GM1 gangliosidosis-affected animals that will produce more than 10 grams of GM1 per kilogram of CNS tissue. For example, GM1 extracted from the cerebrum may exceed 10 grams of GM1 per kilogram of cerebral tissue. In another example, GM1 extracted from the cerebellum may exceed 10 grams of GM1 per kilogram of cerebellar tissue. It should be noted herein that USDA guidelines require an ante mortem inspection. Animals showing neurologic signs are not allowed in inspected meat channels. Currently these animals can undergo custom slaughter resulting in meat being labeled not for resale. Therefore, an animal that is able to retain robustness (e.g. having minimal GM1 gangliosidosis symptoms) while still accumulating high amounts of GM1 in the CNS is of great importance.

In another embodiment, the selective breeding method will involve ovine animals that may originate from the export category flock of the USDA Scrapie Free Certification Program (SFCP). In another embodiment, the ovine animals may also originate from a different scrapie-free certification program. In another embodiment, the ovine animals may also originate from USDA-like scrapie certification programs from other countries, including, but not limited to, the Canadian Voluntary Scrapie Flock Certification Program, the Australian TSE Freedom Assurance Project, or other national scrapie certification program.

In another embodiment, the abattoir guidelines used in the harvest of selectively bred ovine animals with a scrapie-resistant and GM1 gangliosidosis-affected genotype will be those propagated by the USDA. In another embodiment, these guidelines will be national abattoir guidelines from other countries (e.g., Canada, Australia, etc.).

In another embodiment, the harvesting of selectively bred ovine animals with a GM1 gangliosidosis affected/scrapie resistance genotype will result in a yield of GM1 from non-CNS tissue that is greater than 2.0 grams per kilogram. The non-CNS tissues include peripheral nervous tissue, solid organs, connective tissue, vasculature, or any other tissue within the ovine animal where GM1 may be extracted.

In another embodiment, a composition comprising a mixed ganglioside product enriched in GM1 is disclosed in accordance with one or more embodiments of the present disclosure. In another embodiment, the ganglioside product enriched in GM1 is extracted from an ovine animal. In another embodiment, the ovine animal is afflicted with GM1 gangliosidosis. In another embodiment, the ovine animal afflicted with GM1 gangliosidosis harbors a scrapie-resistant genotype (gg/RR). In another embodiment, the GM1 gangliosidosis affected/scrapie-resistant (gg/RR) ovine animal may originate from a flock monitored by the USDA Scrapie Free Flock Certification Program (SFCP).

The composition may be delivered in any manner known in the art. In one embodiment, the composition is formulated for intranasal delivery. In another embodiment, the composition is formulated for intramuscular delivery. In another embodiment, the composition is formulated for subcutaneous delivery. In another embodiment, the composition is formulated for intravenous delivery. In another embodiment, the composition is formulated for intrathecal delivery, intraspinal delivery, or any other delivery method that involves the delivery of the composition into the CNS.

Figure 4:
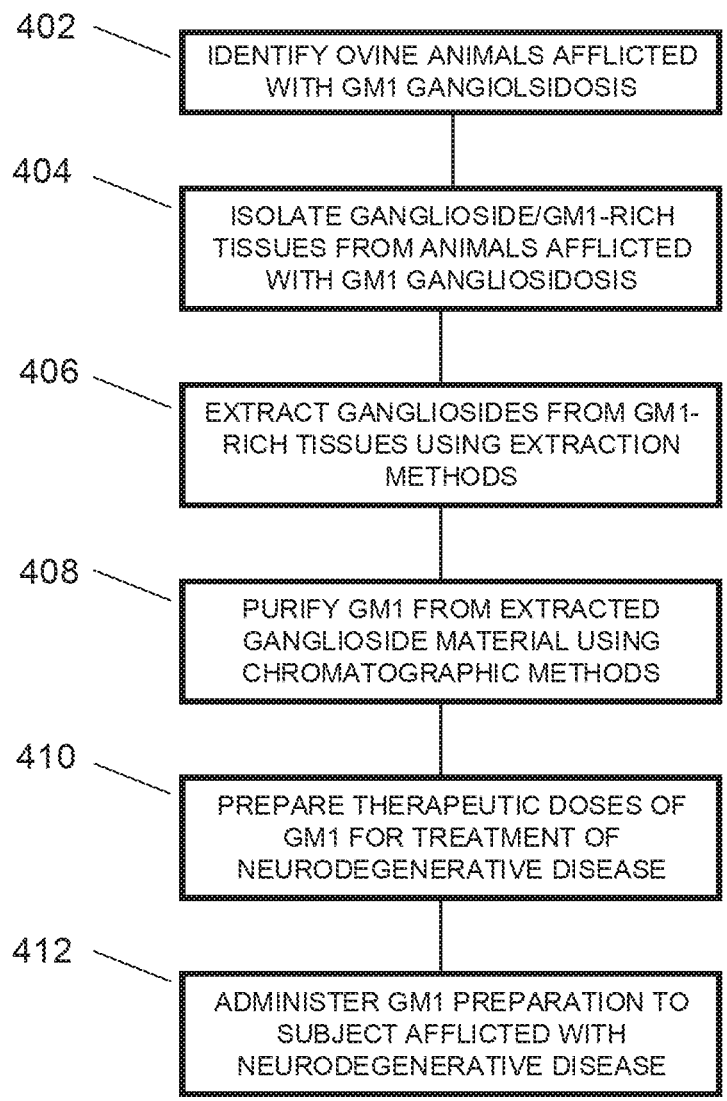
FIG. 4 illustrates a process flow diagram of a method for reducing the levels of a neurodegenerative disease-associated protein in a mammal subject, in accordance with the present disclosure

Referring generally to FIG. 4, a method 400 of reducing the levels of a neurodegenerative disease-associated protein in a mammal subject is disclosed, in accordance with one or more embodiments of the present disclosure. Aggregation of proteins is a hallmark of many neurodegenerative diseases. For example, Huntington's disease is characterized by deposits of aggregated mutated huntingtin protein (mHTT) within the CNS. Reduction or removal of aggregated protein deposits, such as aggregated mHTT, may be facilitated by compounds that increase the solubility of the protein, preventing aggregation or oligomerization. The examples and data below support the idea that GM1 may facilitate the solubility of proteins prone to aggregation, the reduction of aberrant aggregate protein formation, and/or the reduction of aberrant protein aggregates in vivo.

The neurodegenerative-disease related protein in the method 400 may include any protein relevant to a neurodegenerative disease that is hallmarked by misfolded or aggregated protein including but not limited to Alzheimer's disease (e.g., tau and/or N-APP protein), Parkinson's disease (e.g., Alpha-synuclein protein), Amyotrophic lateral sclerosis (e.g., TDP-43 protein), and other amyloidosis diseases. In one embodiment, the method 400 reduces or inhibits the formation of an aggregated protein that is a hallmark of a neurodegenerative disease (e.g., aggregated and/or oligomeric huntingtin protein). In another embodiment, the method 400 reduces the amount of soluble protein that is a known precursor of an aggregated or oligomeric form that is a hallmark of a neurodegenerative disease (e.g., serum levels of soluble mutated huntingtin protein). In an embodiment, the method 400 decreases the aggregation and/or aggregation rate of neurodegenerative disease-associated protein. In another embodiment, the method 400 solubilizes a portion of the aggregate formed by the neurodegenerative disease-associated protein. In embodiments, the method 400 may be performed prophylactically, before the mammal subject exhibits symptoms of neurodegenerative disease.

In an embodiment, the method 400 includes the step 402 of identifying an ovine animal afflicted with GM1 gangliosidosis. In another embodiment, the method 400 includes the step 404 of isolating ganglioside rich tissues from an animal afflicted with gangliosidosis. In another embodiment, the method includes the step 406 of extracting gangliosides from GM1-tissues using extraction methods. In another embodiment, the method 400 includes the step 408 of purifying GM1 from the extracted ganglioside material using chromatographic or other methods. In another embodiment, the method 400 includes the step 410 of preparing therapeutic doses of GM1 for treatment of neurodegenerative disease. In another embodiment, the method 400 includes the step of administering the GM1 preparation to a subject afflicted with a neurodegenerative disease. The steps of tissue isolation, ganglioside extraction, GM1 purification, GM1 preparation and administration have been previously described herein.

In an embodiment, the administration of the ganglioside preparation substantially enriched in GM1 in the method 400 includes at least one of intramuscular, subcutaneous, intranasal, intrathecal, intraspinal, or intravenous delivery.

In an embodiment, the ganglioside preparation substantially enriched in GM1 administered in the method 400 reduces at least one symptom of neurodegenerative disease. The symptoms of neurodegenerative disease may include at least one of a cognitive symptom, and neuromuscular symptom, or a neuropsychiatric symptom. For example, a neuromuscular symptom may include but not be limited to ataxia, hypokinesia, dystonia, or chorea. In another example, a cognitive symptom may include but not be limited to dementia, delusion, or amnesia. In another example, a neuropsychiatric symptom may include but not be limited to anxiety, depression, aggression, or compulsive behavior.

Example 1

Effect of Five-Day Subcutaneous Delivery of Ovine GM1 on Soluble Mutant Huntingtin Protein in R6/2 Transgenic HD Mice Ovine GM1 was tested on R6/2 HD mice. The R6/2 mice express a N-terminal fragment (exon 1) of human huntingtin protein (e.g., a mutant HTT, or mHTT) containing a polyglutamine tract (e.g., greater than 40 glutamine residues) and exhibit many progressive behavioral and neuropathological features observed in HD patients, including choreiform-like movements, involuntary stereotypic movements, tremor, weight loss and striatal cortical neurodegeneration, and have a life span of 3-4 months. These mice also express normal (e.g., wild-type) HTT. Proof-of-concept studies in R6/2 mice have been the foundation of most human clinical trials for medications being examined for their potential to slow the progression of HD. GM1 was administered subcutaneously to 8-week-old R6/2 HD mice at the dose rate of 50 mg/kg twice daily for 5 days and the response of treatment on the both HTT and mHTT levels was determined by HTRF assay as described below. To ensure homogeneity of experimental cohorts, mice from the same F generation were systemically assigned to experimental groups such that age, weight, and CAG-repeat lengths are balanced. The mice were identified by the originally assigned code so that the subsequent studies were performed blind as to the genetic identity of the mice.

Figure 5:
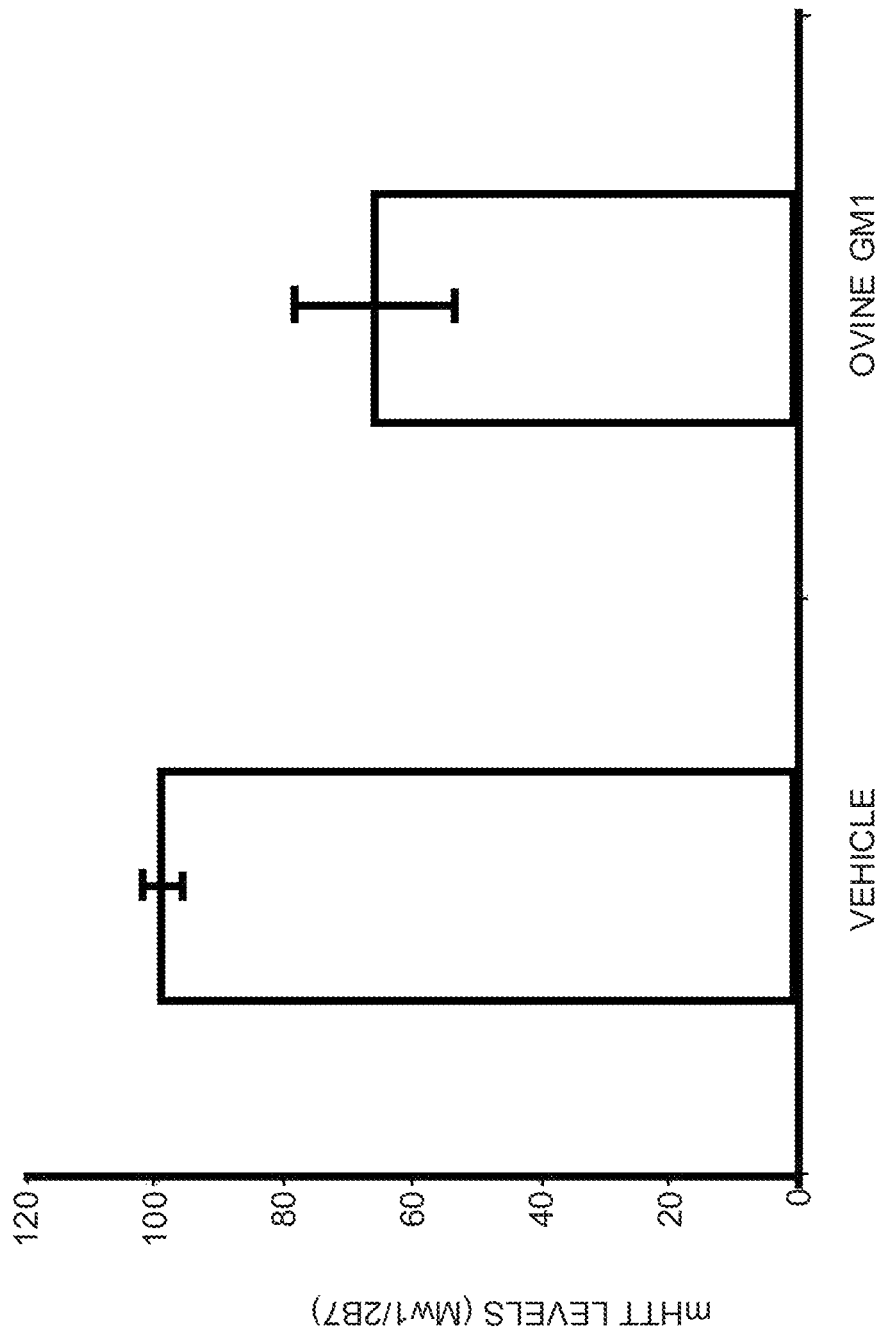
FIG. 5 is a graph illustrating the reduction of mutant huntingtin in GM1 treated mice, in accordance with the present disclosure.

A homogeneous time resolved fluorescence (e.g., HTRF) assay for the measurement of soluble HTT levels in brain tissues was developed. The monoclonal antibodies used in this HTRF assay are specific for selected epitopes on the HTT molecule. The antibodies include: 2B7 monoclonal antibody (e.g., Novartis, Switzerland) specific for the first N-17 amino acids of HTT and mHTT, MW1 MoAb15 (e.g., Developmental Studies Hybridoma Bank, University of Iowa) binds preferentially to expanded polyglutamine sequences (e.g., polyQ), hence binds to mHTT and to a lesser extent to HTT and 2166 MAb (e.g., Millipore Corp, Cat #MAB2166), which binds to the HTT epitope starting at aa 443-457 and recognizes HTT. In brief, brain tissue lysate is mixed with a reaction buffer containing Tb, Alexa488, or D2 fluorophore conjugated antibodies (e.g., 2B7-Tb, MW1-Alexa488 and MAB2166-D2, respectively) and the HTRF signal is read on VICTORX5 plate reader (e.g., Perkin Elmer) after 2 hours of incubation at 40 C. After excitation of the Tb donor at 320 nm, emission signals of Alexa488 and D2 is detected at 510 and 665 nm respectively. The signal resulted from the emission of the Tb is measured at 615 nm and is used for normalization of potential signal artifacts. The relative mHTT and total HTT concentration is represented by the 510/615 nm and 665/615 nm ratios. The assay is performed and recorded according to a GLP compliant SOP, FIG. 5 is a graph illustrating the reduction of mutant huntingtin in GM1 treated mice, in accordance with the present disclosure. Here, a 33% reduction in mutant huntingtin levels with subcutaneously delivered ovine GM1 was determined.

Example 2

Effect of 14-Day Subcutaneous Delivery of Ovine GM1 on Soluble Mutant Huntingtin Protein in R6/2 Transgenic HD Mice In this study, GM1 was administered subcutaneously to 6-week-old R6/2 HD mice at the dose of 25 mg/kg or 50 mg/kg twice daily for 2 weeks and the response of treatment on the body weight, motor function and mutant huntingtin (mHTT) levels was determined. Equal number of male and female mice were used for the study. To ensure homogeneity of experimental cohorts, mice from the same F generation were systemically assigned to experimental groups such that age, weight, and CAG-repeat lengths were balanced. The mice were identified by the originally assigned code so that the subsequent studies were performed blind as to the genetic identity of the mice. All mice were weighed weekly at the same time each day. The decline in motor function and endurance in R6/2 mice were determined using rotarod performance tests and grip strength studies. After the end of the treatment period, animals were sacrificed and brain tissues were processed for biochemical assays as described (e.g., for HTRF studies, soluble HTT and mHTT levels were measured as described in example 1).

For rotarod performance tests, an accelerating rotarod (e.g., from Columbus Instruments, Columbus, Ohio) was used. The mice were trained for one day, then tested with one test per day at each measurement time point. The testing protocol was performed weekly. Grip strength tasks were performed using a digital force gauge (e.g., a Chatillon Ametek Digital Force Gauge, model DFIS 2, from Columbus Instruments). Three consecutive tests were performed for each mouse and the average used for statistical analysis.

For measurements of oligomeric (e.g., aggregate) mHTT, a Meso Scale Discovery (e.g., MSD) assay was utilized. The MSD assay detects mHTT oligomers in brain tissue, CSF and plasma. Using this assay, the effect of GM1 on oligomeric mHTT in cortical tissue of HD mice was measured. In brief, MSD 96 well plates, were coated with 100 ng/well of the capture antibody-mouse anti-mHTT MW8 (e.g., specific for mHTT aggregates) and incubated overnight at 4° C. The plate was washed three times with 0.05% Tween, then blocked at RT for 1 hour with 3% BSA. Brain lysate was added at 25 μg/30 μL, and incubated overnight at 4° C. The detection antibody includes Rb1-AL55 (HTT1-17) and the Goat anti-Rabbit-Ruthenium/Sulfo-Tag. After one hour of incubation at room temperature read buffer was added and the plate was imaged on an MSD instrument (e.g., a QuickPlex SQ120). Every plate included a background control and a set of quality control samples.

Figure 6A:
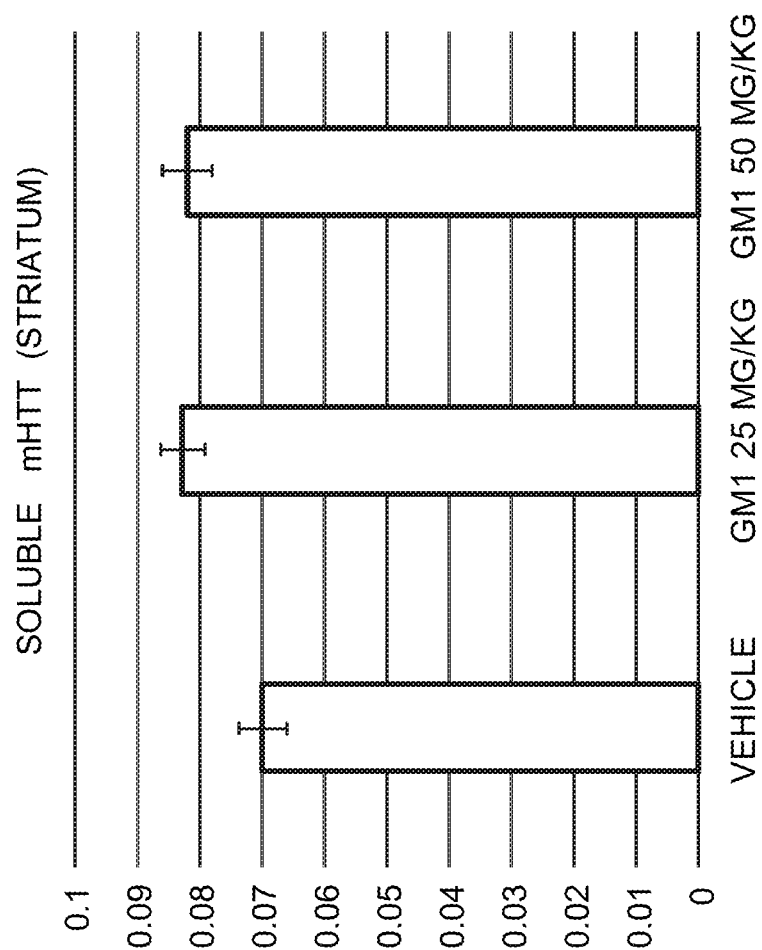
FIG. 6A is a graph illustrating the effect of GM1 treatment on the relative amount of soluble mHTT in the striatum, in accordance with the present disclosure.
Figure 6B:
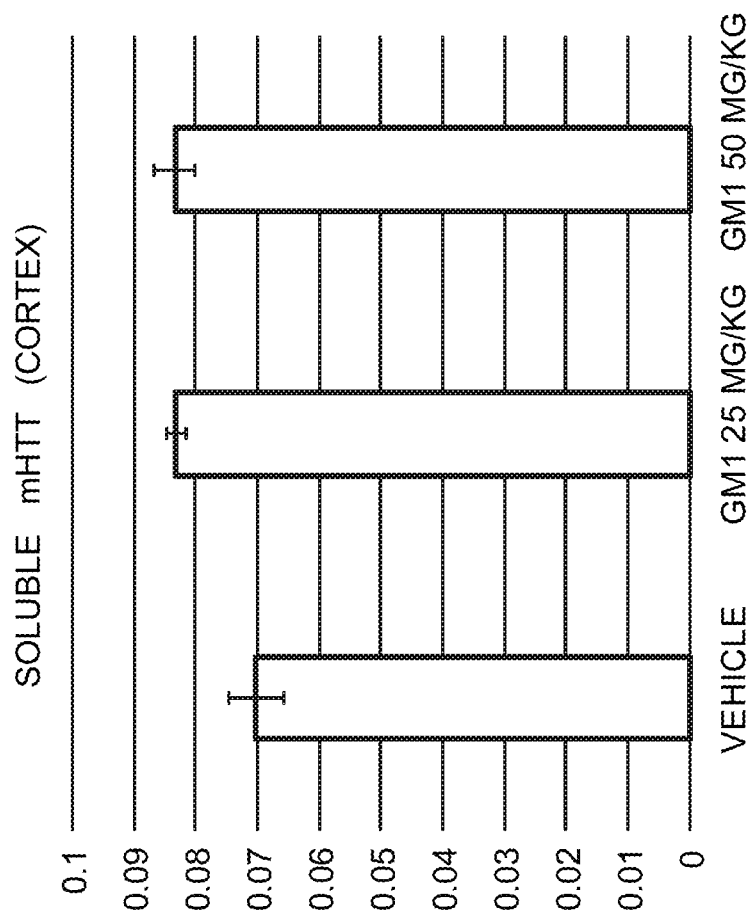
FIG. 6B is a graph illustrating the effect of GM1 treatment on the relative amount of soluble mHTT in the cortex, in accordance with the present disclosure.
Figure 6C:
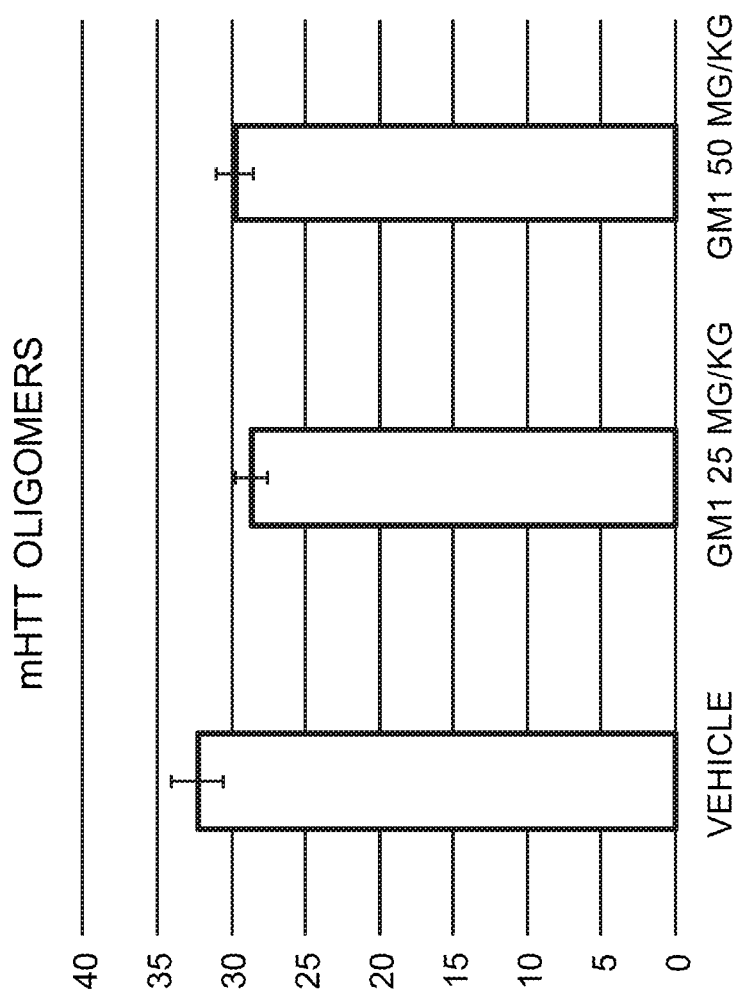
FIG. 6C is a graph illustrating the effect of GM1 treatment on the amount of aggregated mHTT in cortical tissue, in accordance with the present disclosure.
Figure 6D:
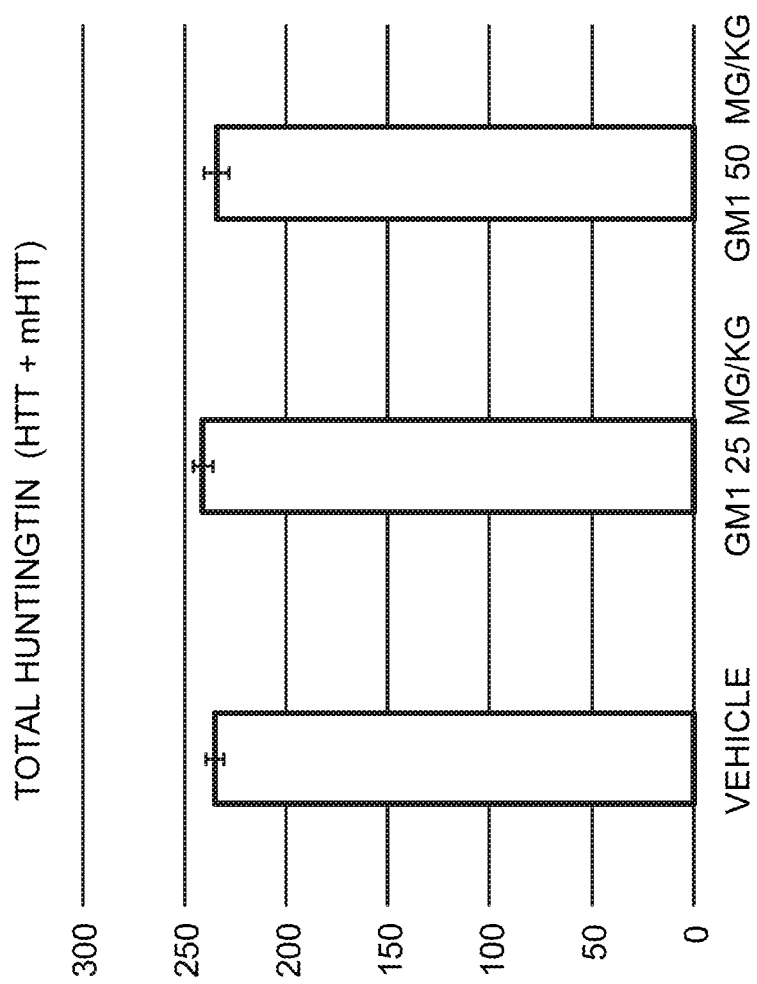
FIG. 6D is a graph illustrating the effect of GM1 treatment on the total amount of HTT in cortical tissue, in accordance with the present disclosure.

FIGS. 6A-6B are graphs illustrating the effect of GM1 treatment on the relative amount of soluble mHTT in the striatum and cortex of the brain, respectively, in accordance with the present disclosure. Increases in soluble mHTT were observed in both striatal and cortical tissue with both 25 mg/kg and 50 mg/kg doses of GM1. FIG. 6C is a graph illustrating the effect of GM1 treatment on the amount of aggregated mHTT in cortical tissue, in accordance with the present disclosure. The aggregated form of HTT contains a mixture of both the transgenic mHTT, HTT, and a mixture of mHTT and HTT cleavage products. In cortical tissue, both 25 mg/kg and 50 mg/kg doses of GM1 reduced aggregated HTT (e.g., mainly mHTT oligomers). Total huntingtin protein (e.g., both mHTT and HTT) in cortical tissue was relatively unchanged, as shown in FIG. 6D. The reduction in aggregated mHTT, the increase in soluble mHTT, and unchanged total huntingtin protein amounts suggests that GM1 decreases the aggregation of harmful huntingtin oligomers in vivo. In other words, GM1 treatment shifted the mHTT equilibrium from the highly toxic oligomeric form to the less toxic soluble form.

Figure 7A:
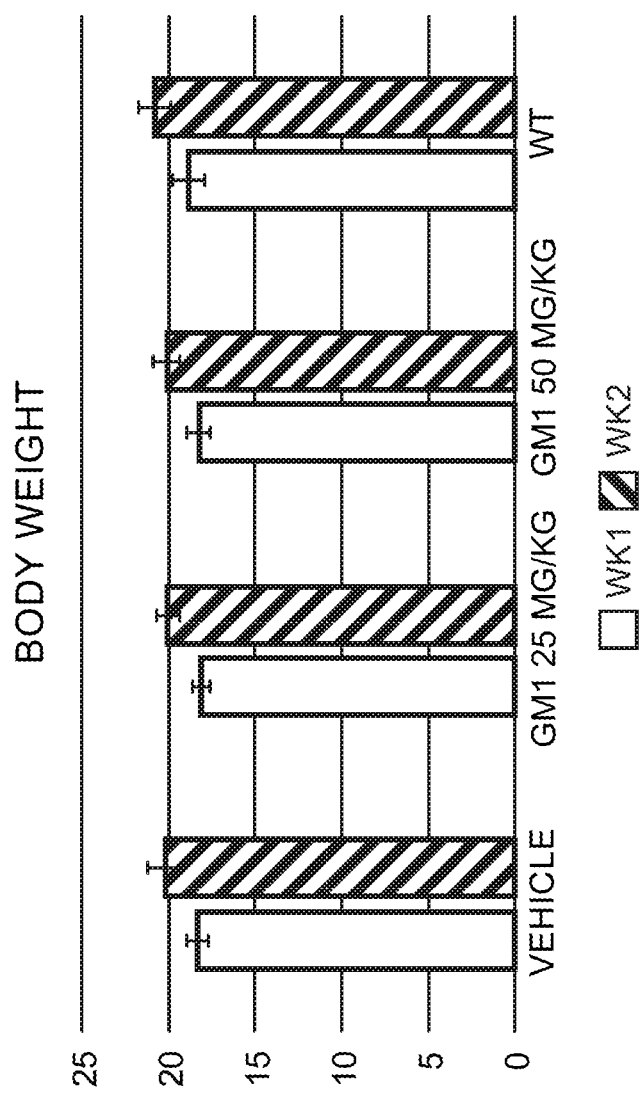
FIG. 7A is a graph illustrating the effect of GM1 treatment on the weight of mice expressing the mHTT, in accordance with the present disclosure.
Figure 7B:
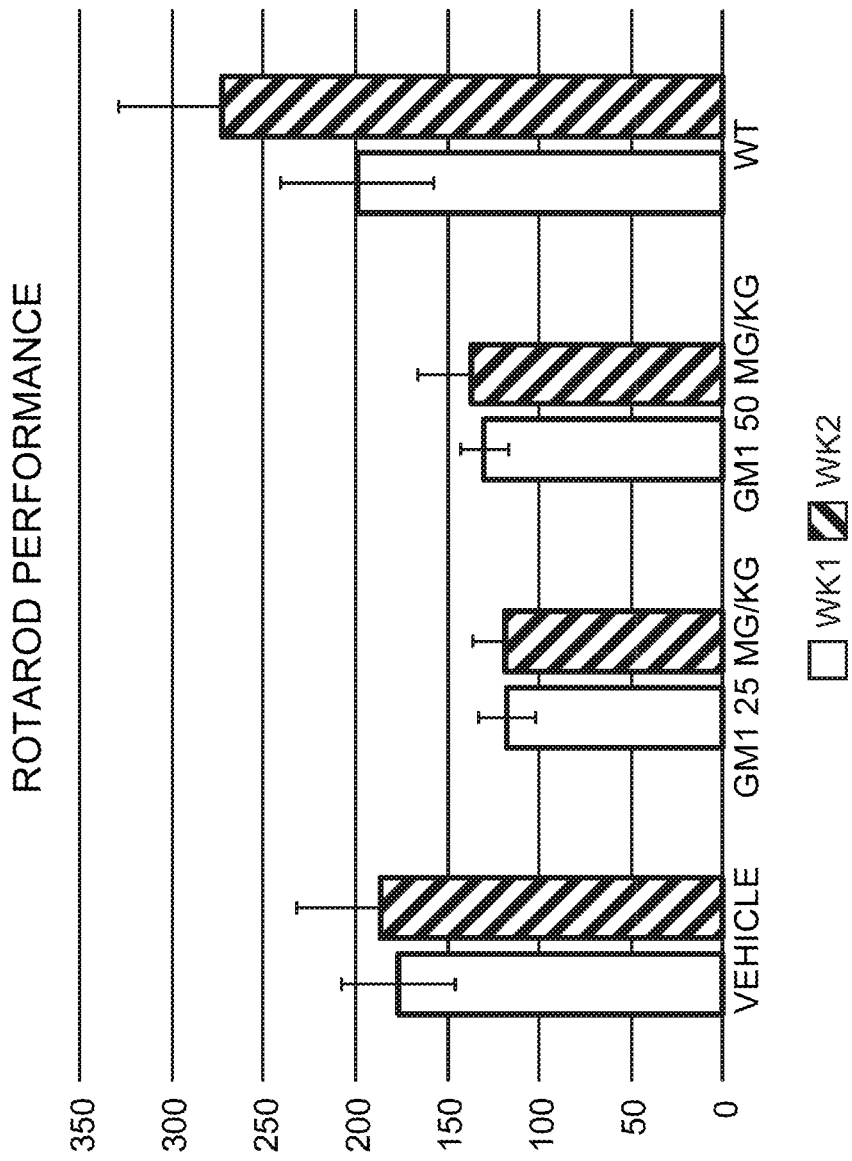
FIG. 7B is a graph illustrating the effect of GM1 treatment on the ability mice expressing the mHTT to perform a rotarod performance test, in accordance with the present disclosure.
Figure 7C:
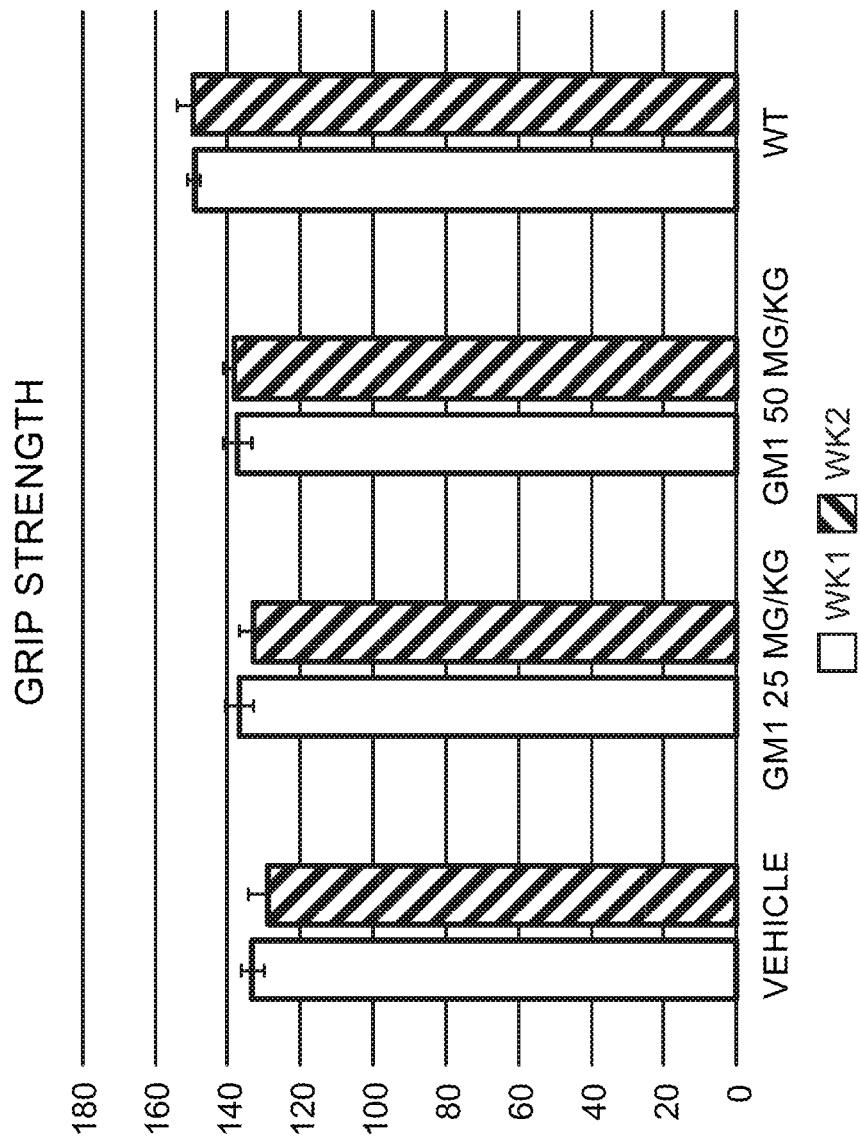
FIG. 7C is a graph illustrating the effect of GM1 treatment on the ability of mice expressing the mHTT to perform a grip strength test, in accordance with the present disclosure.

FIGS. 7A-7C are graphs illustrating the effect of GM1 treatment on weight and performance of mice expressing the transgenic mHTT in accordance with the present disclosure. Both the 25 mg/kg and 50 mg/kg subcutaneous treatments of GM1 had little to no effect on the weight of the animal after 14 days of treatment, as shown in FIG. 6A, indicating that GM1 is well tolerated. The baseline performance of the GM1 treated animals were somewhat lower than the vehicle treated animals in the rotarod experiments (e.g., as shown in FIG. 6B), however, all groups were nearly identical in the grip strength experiments, as shown in FIG. 6C. Taken together, these results show that subcutaneous treatment of GM1 has little negative effect on the viability and activity on a mice model for Huntington's disease. It should be noted that an improvement in activity should not be expected in GM1 animals, as the time course of 14 days is likely insufficient for any improvement to be seen.

The present disclosure has been illustrated in detail with reference to specific examples. It is to be noted that the examples should not be interpreted as a limitation of the present disclosure, but merely as an illustration.

The present disclosure has been particularly shown and described with respect to certain embodiments and specific features thereof. The embodiments set forth herein are taken to be illustrative rather than limiting. It should be readily apparent to those of ordinary skill in the art that various changes and modifications in form and detail may be made without departing from the spirit and scope of the disclosure.

What is claimed:

1. A method of treating a symptom of Huntington's disease in a mammal subject, comprising:

preparing a ganglioside preparation enriched in GM1 by:

isolating ganglioside-rich tissues from one or more ovine animals afflicted with GM1 gangliosidosis and harboring a scrapie-resistant genotype;

extracting of gangliosides, including GM1, from the ganglioside-rich tissues using extraction methods and extraction reagents; and purifying GM1-enriched gangliosides from the extracted gangliosides though chromatographic methods; and administering to the mammal subject a therapeutic quantity of the ganglioside preparation enriched in GM1 to treat Huntington's disease within the mammal subject.

2. The method of claim 1, wherein the ovine animal harboring a scrapie-resistant genotype originates from a flock monitored by the USDA Scrapie Free Flock Certification Program (SFCP) or similar scrapie-related program.

3. The method of claim 2, wherein administering comprises at least one of intramuscular, subcutaneous, intranasal, intrathecal, intraspinal, or intravenous delivery.

4. The method of claim 1, wherein the symptom of Huntington's disease is a least one of: cognitive symptoms, neuromuscular symptoms, or neuropsychiatric symptoms.

5. The method of claim 4, wherein the cognitive symptoms are at least one of dementia, delusion, and amnesia.

6. The method of claim 4, wherein the neuromuscular symptoms are at least one of ataxia, hypokinesia, dystonia, and chorea.

7. The method of claim 4, wherein the neuropsychiatric symptoms are at least one of anxiety, depression, aggression and compulsive behavior.

* * * * *